(12) United States Patent
Valtchev

(10) Patent No.: US 6,527,793 B1
(45) Date of Patent: Mar. 4, 2003

(54) LAPAROSCOPIC NEEDLE INTRODUCER DEVICE

(76) Inventor: Konstantin L. Valtchev, 600 Sherbourne St., Suite 507, Toronto Ontario (CA), M4X 1W4

(*) Notice: Subject to any disclaimer, the term of this patent is extended or adjusted under 35 U.S.C. 154(b) by 167 days.

(21) Appl. No.: 09/663,910

(22) Filed: Sep. 18, 2000

(51) Int. Cl.$^7$ ............................................. A61B 17/06
(52) U.S. Cl. ..................................... 606/222; 606/139
(58) Field of Search ................................ 606/222, 223, 606/224, 139, 144, 145, 148

(56) References Cited

U.S. PATENT DOCUMENTS

| | | | |
|---|---|---|---|
| 5,129,912 A | * 7/1992 | Noda et al. ................... 289/1.2 |
| 5,306,254 A | * 4/1994 | Nash et al. ................... 600/585 |
| 5,320,632 A | * 6/1994 | Heidmueller ............... 112/169 |
| 5,403,328 A | * 4/1995 | Shallman ................... 606/144 |
| 5,549,618 A | * 8/1996 | Fleenor et al. ............... 112/169 |
| 5,573,542 A | * 11/1996 | Stevens ....................... 112/169 |
| 5,626,588 A | * 5/1997 | Sauer et al. ................. 112/169 |
| 5,628,757 A | * 5/1997 | Hasson ........................ 606/139 |
| 5,904,692 A | * 5/1999 | Steckel et al. ............... 128/898 |
| 5,908,426 A | * 6/1999 | Pierce ........................ 606/139 |
| 6,113,610 A | * 9/2000 | Poncet ........................ 128/898 |
| 6,206,893 B1 | * 3/2001 | Klein et al. .................. 606/139 |
| 6,221,084 B1 | * 4/2001 | Fleenor ....................... 606/148 |
| 2001/0053916 A1 | * 12/2001 | Rioux ........................ 606/139 |

* cited by examiner

*Primary Examiner*—David O. Reip
*Assistant Examiner*—D Jacob Davis
(74) *Attorney, Agent, or Firm*—Sturm & Fix LLP

(57) ABSTRACT

A device (10) for introducing and removing a laparoscopic needle (200) through an incision (301) in a wall (302) of a body cavity (300) wherein the device (10) comprises a rod unit (11) including an elongated rod member (20) having a proximal (21) and a distal (22) end segment disposed on the opposite ends of an interior chamber (34) provided with an elongated slot (33) dimensioned to receive a curved laparoscopic needle (200) and a handle member (40) for manipulating the position of the laparoscopic needle (200) within the body cavity (300). In one version of the preferred embodiment, the curved needle (200) is releasably engaged between the tubular proximal end segment (21") and distal end (51) of the elongated slot (33') of the rod member (20').

9 Claims, 4 Drawing Sheets

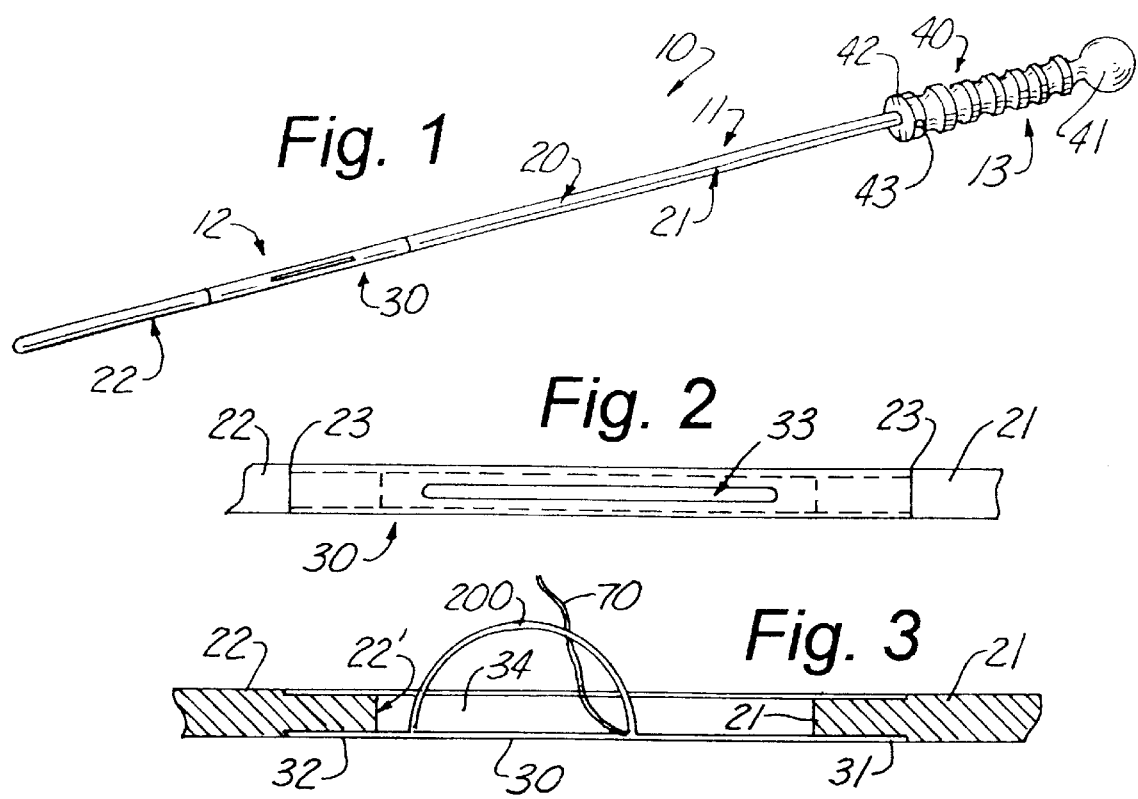
Fig. 1
Fig. 2
Fig. 3
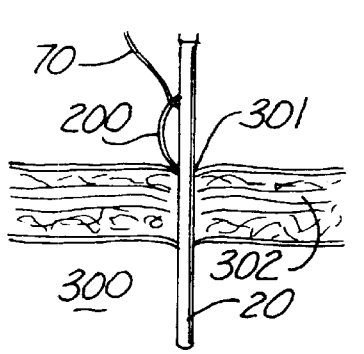
Fig. 4A
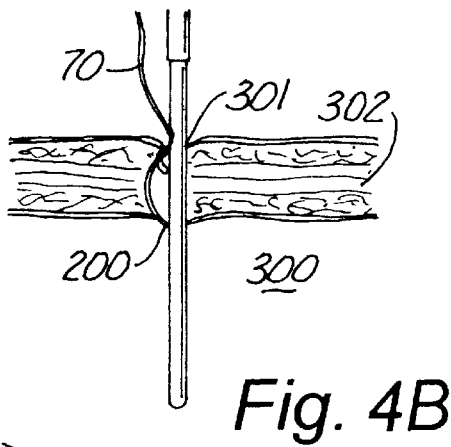
Fig. 4B
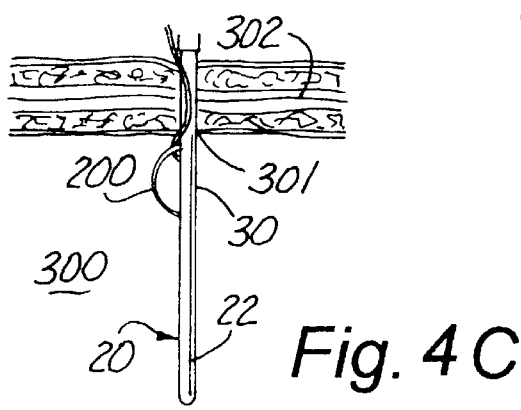
Fig. 4C

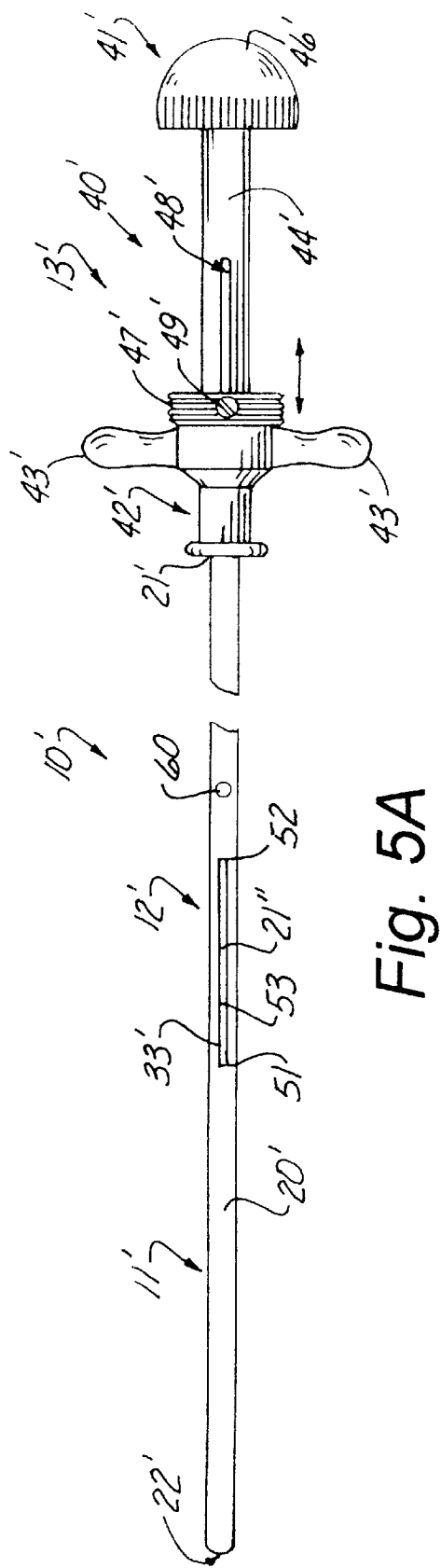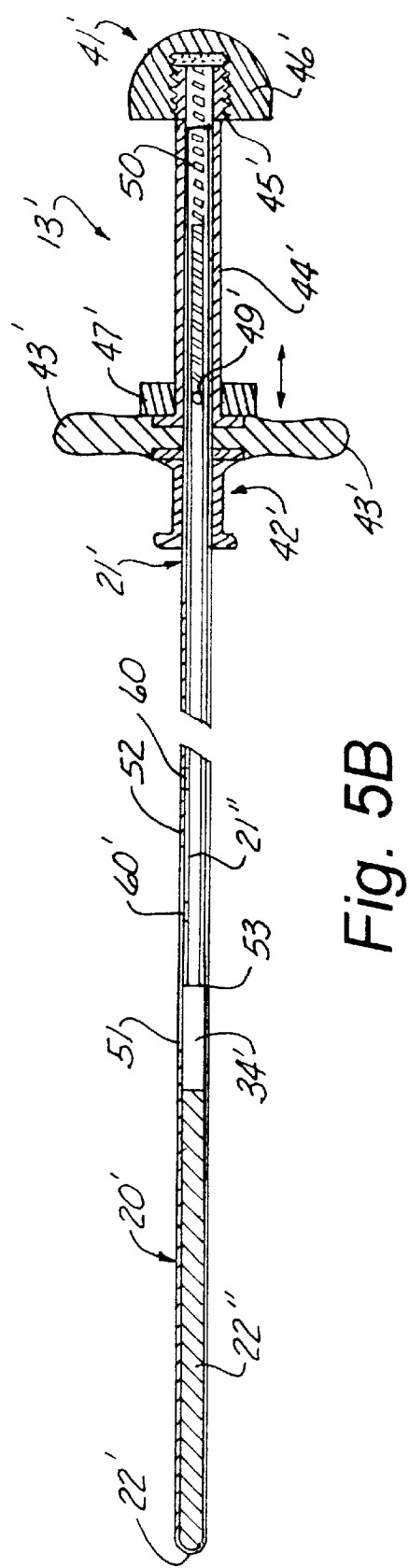
Fig. 5A
Fig. 5B

LAPAROSCOPIC NEEDLE INTRODUCER DEVICE

BACKGROUND OF THE INVENTION

1. Field of the Invention

The present invention relates to the field of surgical implements in general, and in particular to a surgical implement used to introduce a curved needle into the peritoneal cavity during laparoscopic surgery.

2. Description of Related Art

There is currently no specialized instrument for the introduction of a curved needle into the peritoneal cavity. Presently, such needles can be introduced through a trocar sleeve with an interior diameter larger than 11 mm. A method developed by Dr. H. Reich enables the surgeon to introduce any size curved needle into the peritoneal cavity through a 5 mm lower quadrant incision. The disadvantage of this method are that insertion of the needle into the abdominal wall, after the removal of the trocar sleeve makes, it is difficult for the surgeon to find the original incision resulting in additional damage as he attempts to follow the original path. Also, the unprotected needle damages the soft tissue through which it is traveling.

As a consequence of the foregoing situation, there has existed a longstanding need among surgeons for a new and improved device for introducing a curved laparoscopic needle into a body cavity in as non-invasive a manner as possible with full control over the positional placement of the needle within the body cavity, and the provision of such a device is a stated objective of the present invention.

BRIEF SUMMARY OF THE INVENTION

Briefly stated, the laparoscopic needle introducer device that forms the basis of the present invention comprises an elongated rod unit having a needle engaging unit for receiving a curved laparoscopic needle and a handle unit for manipulating the rod unit within a body cavity and releasably engaging the needle from the needle engaging unit.

As will be explained in greater detail further on in the specification, the basic rod unit includes an elongated rod member having a proximal rod segment and a distal rod segment disposed on the opposite ends of a needle engaging unit which comprises an interior chamber formed on an intermediate portion of the rod member. The interior chamber is provided with an elongated slot dimensioned to receive a curved laparoscopic needle.

In the first version of the invention, the length of the interior chamber is fixed, and the proximal rod segment of the rod member is fixedly secured to the handle unit, which includes a handle member having a proximal end and a distal end.

However, in the second version of the invention, the rod unit comprises an elongated hollow tubular rod member having a fixed distal rod segment and a moveable proximal rod segment which define a variable length interior chamber that positively, yet releasably engages the laparoscopic needle via a spring biased arrangement that is carried on a hollow stem on the handle member and operatively connected to the proximal rod segment of the hollow tubular rod member to vary the effective length of the interior chamber.

In addition, the second version of the invention is further provided with a pair of discrete alignable apertures that are dimensioned to receive and captively engage the opposite ends of a length of surgical thread that had previously been attached to the laparoscopic needle to allow a surgeon to tie surgical knots in the length of thread in an extra corporeal fashion.

In order to accomplish this function, the discrete apertures are aligned with the slot in the elongated rod member and one of the apertures is formed in the proximal end of the elongated rod member. The other aperture is formed in the moveable proximal rod segment which is operatively connected to the spring biased arrangement on the handle member such that the apertures can be moved into and out of alignment with one another to captively engage and release the opposite ends of the surgical thread.

BRIEF DESCRIPTION OF THE SEVERAL VIEWS OF THE DRAWINGS

These and other attributes of the invention will become more clear upon a thorough study of the following description of the best mode for carrying out the invention, particularly when reviewed in conjunction with the drawings, wherein:

FIG. 1 is a perspective view of the first version of the preferred embodiment of the laparoscopic needle introducer device;

FIG. 2 is an isolated top plan view of the needle engaging unit of the first version of the preferred embodiment;

FIG. 3 is a cross sectional view of the needle engaging unit;

FIGS. 4A through 4C illustrate the progressive insertion of the curved needle through a laparoscopic incision;

FIGS. 5A and B are a top plan and top plan cross sectional view, respectively, of the second version of the preferred embodiment of the laparoscopic needle introducer device that forms the basis of the present invention with the retractable ring element fully extended;

DETAILED DESCRIPTION OF THE INVENTION

Figure 6:
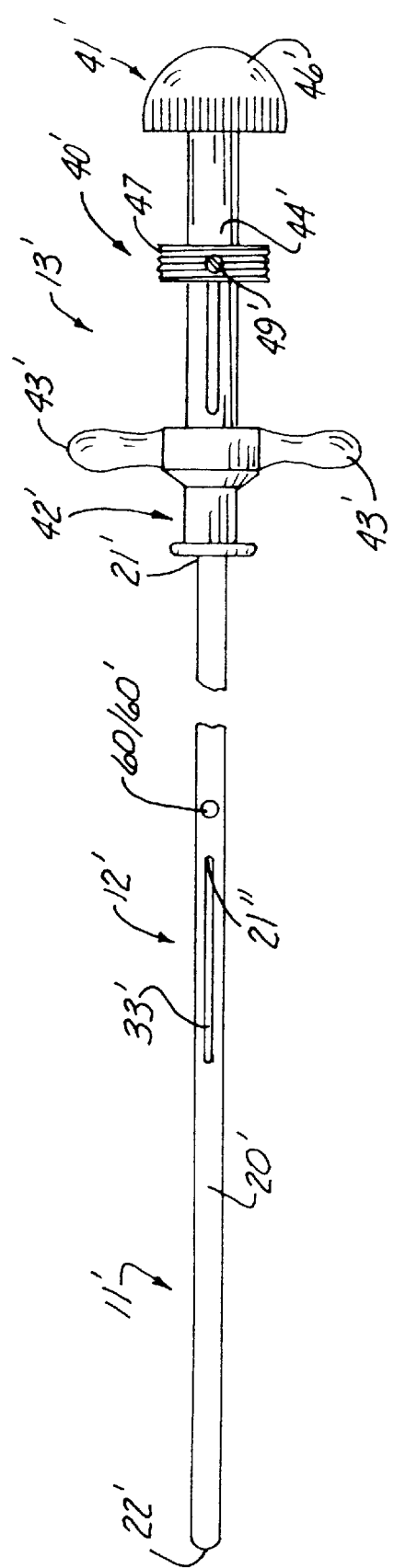
FIG. 6 is a top plan view of the second version of the preferred embodiment with the retractable ring element fully retracted.

As can be seen by reference to the drawings, and in particular to FIG. 1, the laparoscopic needle introducer device that forms the basis of the present invention is designated generally by the reference number 10. The device 10 comprises in general a rod unit 11, a needle engaging unit 12, and a handle unit 13. These units will now be described in seriatim fashion.

In the first version of the preferred embodiment depicted in FIGS. 1 through 3, it can be seen that the rod unit 11 comprises an elongated rod member 20 including an elongated proximal solid rod segment 21 and a shorter distal rod segment 22. The opposed ends 21', 22' of each of the solid rod segments 21, 22 are provided with a reduced diameter stepped shoulder 23 whose purpose and function will be described presently.

As can best be seen by reference to FIGS. 2 and 3, the needle engaging unit 12 comprises a hollow tubular sleeve 30 having opposite ends 31, 32 which are fixedly secured to the opposite ends 21', 22' of the proximal 21 and distal 22 solid rod segments 21, 22. The intermediate portion of the sleeve 30 is provided with an elongated slot 33 that is dimensioned to receive the opposite ends of a curved laparoscopic needle 200 into the interior chamber 34 within the, hollow tubular sleeve 30.

Furthermore, as shown in FIG. 1, the handle unit 13 includes an elongated contoured handle member 40 having a proximal end 41 and a distal end 42. The distal end 42 of the handle member 40 is fixedly secured to the proximal solid rod segment 21 of the rod member 20 and further provided with a discrete knob element 43 which is aligned with the elongated slot 33 of the needle engaging unit 12 to assist the surgeon in manipulating the position of the needle 200 within a body cavity 300 as will be explained in greater detail further on in the specification.

In the second version of the preferred embodiment of the device 10' illustrated in FIGS. 5A and 5B, the rod unit 11' comprises an elongated hollow tubular rod member 20' having a closed distal end 22' dimensioned to receive a solid distal rod segment 22" and an open proximal end 21' which is dimensioned to receive a moveable tubular proximal rod segment 21". The distal end 53 of the tubular rod 21", in combination with the distal end 51 of the elongated slot 33', cooperate to define a variable length interior chamber 34', provided with an elongated slot 33' that is dimensioned to receive a curved laparoscopic needle (not shown). The elongated slot 33' and the variable length interior chamber 34' define the needle engaging unit 12' of the second version of the preferred embodiment.

As can best be seen by reference to FIG: 5B, the handle unit 13' comprises a handle member 40' having a distal unit 42' which is fixedly secured to the open proximal end 21' of the tubular rod member 20'. The distal end 42' of the handle member 40' has a plurality of outwardly extending arm elements 43', the intermediate portion of the handle member 40' has an elongated hollow stem 44' which terminates in a threaded proximal end 45' that is engaged by a removal cap element 46'.

Turning now to FIGS. 5A, 5B and 6, it can be seen that in the second version of the preferred embodiment, the handle member 40' is also provided with a retractable ring element 47' which is slidably disposed on the hollow stem 44' which is further provided with an elongated slot 48' that is aligned with the slot 33' in the rod member 20' for reasons that will be explained presently.

As can also be seen by reference to FIGS. 5A and 5B, the retractable ring element 47' is further provided with a fastener element 49' which extends through the elongated slot 48' in the hollow stem 44' of the handle member 40' and is fixedly secured to the tubular proximal end segment 21" that is slidably disposed in the elongated hollow tubular rod member 20'.

In addition, the interior of the hollow stem 44' of the handle member 40 is further provided with a spring element 50' which biases the tubular proximal end segment 21" away from the threaded cap element 46' to force the tubular proximal end segment 21" towards the distal end 51 of the elongated slot 33' within the rod member 20' to reduce the effective size of the interior chamber 34' within the rod member 20'.

By now it should be appreciated that when a surgeon wishes to captively engage a curved needle 200 within the second version of the device 10', it will first be necessary to grasp the retractable ring element 47' and retract the ring element 47' in the direction of the cap element 46'. The fastener element 49' will slide within the elongated slot 48' in the elongated stem 44' of the handle member 40'.

The surgeon would then insert the ends of a curved needle into the slot 33' in the rod member 20' and release the slidable ring element 47' so that the spring element 50 will captively engage the curved needle 200 between the proximal end segment 21" and the distal end 51 of the elongated slot 33' within the rod member 20'.

Turning now to FIGS. 4A through 4C, it can be seen that in both versions of this invention, the curved needle 200 is inserted into a body cavity 300 by passing the rod member 20 through an incision 301 made in the body cavity wall 302. The curved needle 200 may be released from the elongated slot 33 formed in the intermediate portion of the rod member 20 once the handle member 40 has been manipulated to place the curved needle 200 at a desired location within the body cavity 300.

Obviously, it should also be appreciated that this procedure can be reversed to remove a needle 200 from within the peritoneal cavity.

Returning once more to FIGS. 5A, 5B, and 6, it can be seen that in the second version of the preferred embodiment, the device 10' is provided with a pair of alignable apertures 60 and 60' whose purpose and function will be explained presently.

The exterior aperture 60 is formed through the rod unit 11' on the tubular rod member 20' proximate the slot 33' and the interior aperture 60' is formed on the movable tubular proximal end segment 21".

As shown in FIG. 6, the interior 60' and exterior 60 apertures are aligned when the retractable ring element 47' is fully retracted towards the cap element 46'.

Figure 7A:
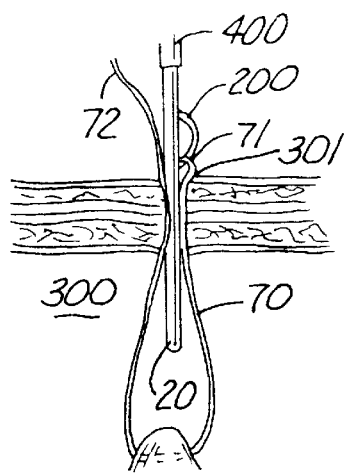
FIGS. 7A through 7E illustrate the use of the device not only to introduce and remove a needle from a peritoneal cavity, but also the capture manipulation and withdrawal of the surgical thread to facilitate the extra corporeal tying of surgical knots.
Figure 7B:
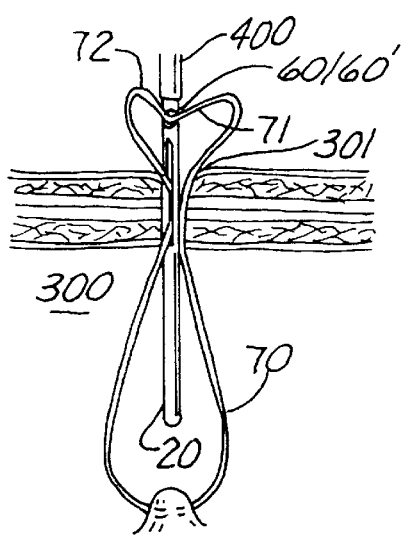
Figure 7C:
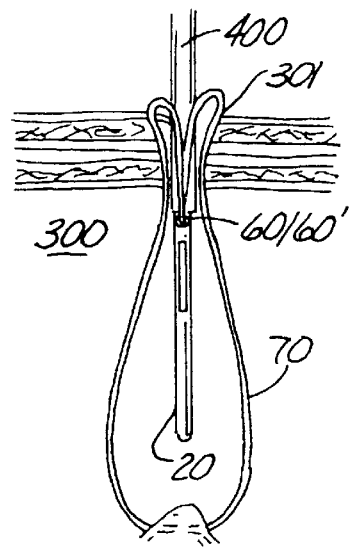
Figure 7D:
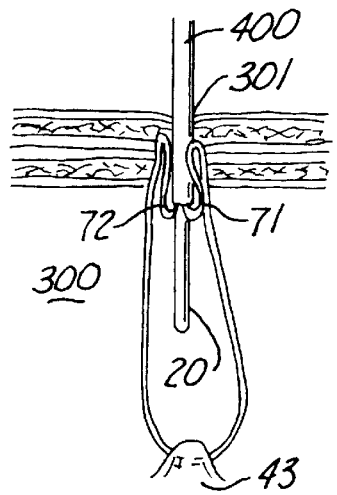
Figure 7E:
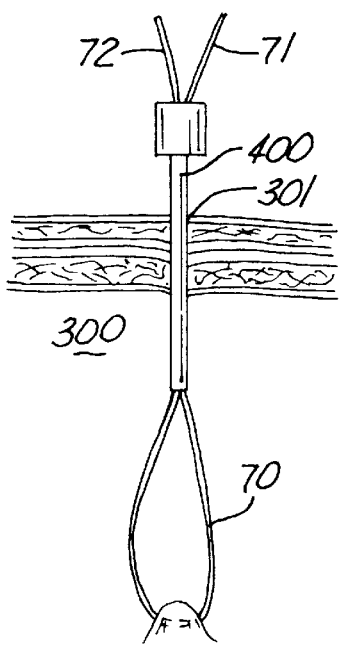

Turning now to FIGS. 7A through 7E, it can be seen that after the device has withdrawn the needle 200 from the peritoneal cavity 300 through the incision 301 (FIG. 7A), the surgical thread 70 can be severed from the needle 200 and both tag ends 71, 72 of the thread can be inserted into the aligned apertures 60, 60' at which point, the retractable ring element 47' would be released to captively engage the tag ends of the thread within the interior of the tubular rod member 20' of the device (FIG. 7B).

At this juncture, the trocar sleeve 400 would be reinserted through the incision 301 (FIG. 7C), and once the lower end of the trocar sleeve 400 entered the peritoneal cavity 300, the device 10' could be withdrawn (FIG. 7D) to totally remove the device 10' from the trocar sleeve 400 wherein the tag ends 71, 72 of the surgical thread 70 wherein the extra corporeal tying of thread 70 by the surgeon can commence.

Although only an exemplary embodiment of the invention has been described in detail above, those skilled in the art will readily appreciate that many modifications are possible without materially departing from the novel teachings and advantages of this invention. Accordingly, all such modifications are intended to be included within the scope of this invention as defined in the following claims.

Having thereby described the subject matter of the present invention, it should be apparent that many substitutions, modifications, and variations of the invention are possible in light of the above teachings. It is therefore to be understood that the invention as taught and described herein is only to be limited to the extent of the breadth and scope of the appended claims.

I claim:

1. A laparoscopic needle introducer device for inserting and removing a curved needle and length of surgical thread into and out of a body cavity wherein the device comprises:

a rod unit including an elongated hollow tubular rod member having a closed distal end, and open proximal end, a proximal rod segment and a distal rod segment; wherein the distal rod segment is fixedly secured in the closed distal end of the tubular rod member and the proximal rod segment has an open ended tubular configuration and is slidably disposed within the open proximal end of the tubular rod member; and, wherein, the proximal rod segment of the tubular rod member is spring biased toward the distal rod segment of the tubular rod member;

a needle engaging unit including an interior chamber formed on the tubular rod member intermediate the proximal and distal rod segments wherein the interior chamber is further provided with an elongated aperture dimensioned to receive the curved needle; and, a handle unit including a handle member operatively associated with the proximal rod segment; wherein, the handle member has a distal end and a proximal end and the open proximal end of the tubular rod member is fixedly secured to the distal end of the handle member which further includes a hollow stem disposed intermediate the distal and proximal ends of the handle member; and, wherein a portion of the proximal rod segment of the tubular rod member is slidably disposed within the hollow stem of the handle member.

2. The device as in clam 1 further including:

means for overcoming the spring biasing of said proximal rod segment toward said distal rod segment.

3. The device as in claim 1 wherein the handle member further includes:

means for moving a portion of the slidable proximal rod segment of the tubular rod member within the hollow stem of the handle member.

4. The device as in claim 1 wherein the handle member includes a retractable ring element slidably disposed on the hollow stem of the handle member wherein the ring element is operatively connected to the proximal rod segment of the hollow tubular rod member.

5. The device as in claim 4 wherein the hollow stem of the handle member is provided with an elongated slot that is dimensioned to receive a fastening element that connects the ring element to the proximal end segment of the hollow tubular rod member.

6. The device as in claim 5 wherein the elongated slot in the hollow stem of the handle member is aligned with the elongated slot that opens into the interior chamber of the needle engaging unit.

7. The device as in claim 5 wherein the proximal rod segment is provided with a first discrete aperture and the elongated rod member is provided with a second discrete aperture wherein said first and second discrete apertures are alignable with one another when the retractable ring element is disposed in its fully retracted mode.

8. The device as in claim 7 wherein said first and second discrete apertures are dimensioned to receive the opposite ends of said length of surgical thread when the retractable ring element is in a partially extended mode.

9. The device as in claim 1, wherein, the handle member has a knob element that is aligned with said elongated aperture.

* * * * *